(12) United States Patent
Choi et al.

(10) Patent No.: US 12,427,107 B2
(45) Date of Patent: Sep. 30, 2025

(54) EYE DROPS CONTAINING CHITOSAN NANOPARTICLES IN WHICH PDRN IS ENCAPSULATED, AND PREPARATION METHOD THEREFOR

(71) Applicant: ZERONE BIO INC., Chungcheongnam-do (KR)

(72) Inventors: Dong Rack Choi, Seongnam-Si (KR); De Zoysa Pathmendrra Mahanama, Daejeon (KR); Thi Thu Thao Nguyen, Suwon-si (KR); Ji Soo Lee, Gyeonggi-Do (KR); Sajith Dananjaya Sirimanna Hettilage, Chungcheongnam-do (KR)

(73) Assignee: ZERONE BIO INC., Chungcheongnam-do (KR)

( * ) Notice: Subject to any disclaimer, the term of this patent is extended or adjusted under 35 U.S.C. 154(b) by 977 days.

(21) Appl. No.: 17/437,290

(22) PCT Filed: Mar. 6, 2020

(86) PCT No.: PCT/KR2020/003203
§ 371 (c)(1),
(2) Date: Nov. 4, 2021

(87) PCT Pub. No.: WO2020/184916
PCT Pub. Date: Sep. 17, 2020

(65) Prior Publication Data
US 2022/0160624 A1    May 26, 2022

(30) Foreign Application Priority Data
Mar. 8, 2019   (KR) .................. 10-2019-0027194

(51) Int. Cl.
| | |
|---|---|
| *A61K 9/00* | (2006.01) |
| *A61K 9/51* | (2006.01) |
| *A61K 31/11* | (2006.01) |
| *B82Y 5/00* | (2011.01) |

(52) U.S. Cl.
CPC .......... *A61K 9/0048* (2013.01); *A61K 9/5161* (2013.01); *A61K 31/11* (2013.01); *B82Y 5/00* (2013.01)

(58) Field of Classification Search
CPC .... A61K 9/0048; A61K 9/5161; A61K 31/11; B82Y 5/00
See application file for complete search history.

(56) References Cited

U.S. PATENT DOCUMENTS

| | | | |
|---|---|---|---|
| 2003/0143166 A1* | 7/2003 | Heger | A61K 8/496 |
| | | | 424/59 |
| 2017/0143011 A1 | 5/2017 | Ahtchi-Ali | |
| 2022/0160624 A1 | 5/2022 | Choi et al. | |

FOREIGN PATENT DOCUMENTS

| | | | | |
|---|---|---|---|---|
| EP | 1859792 A1 * | 11/2007 | ........... | A61K 31/722 |
| EP | 2792375 A1 * | 10/2014 | ............ | A61L 27/20 |
| EP | 2792375 B1 | 11/2015 | | |
| KR | 10-2004-0020679 A | 3/2004 | | |
| KR | 10-2008-0019014 A | 2/2008 | | |
| KR | 10-2014-0055205 A | 5/2014 | | |
| KR | 20140055205 A * | 5/2014 | | |
| KR | 102034982 B1 | 10/2019 | | |

OTHER PUBLICATIONS

Squadrito et al.; Pharmacological Activity and Clinical Use of PDRN; CrossMark; Frontiers in Pharmacology Apr. 2017 | vol. 8 | Article 224 1-7 (Year: 2017).*
Tonello et al.; Characterization and quantitation of the active polynucleotide fraction (PDRN) from human placenta, a tissue repair stimulating agent; Elsevier; Journal of Pharmaceutical and Biomedical Analysis 14 (1996) 1555-1560 (Year: 1996).*
https://getglowingnowskincare.com/blog/the-facts-on-pdrn-and-skin-regeneration/#:~:text=PDRN%2C%20or%20polydeoxyribonucleotide%2C%20has%20become,the%20DNA%20in%20salmon%20sperm. site accessed Jun. 2024 (Year: 2022).*
Machine translation of KR-20140055205-A (Year: 2014).*
International Search Report and Written Opinion for International Application No. PCT/KR2020/003203 dated Jun. 24, 2020.
Ludwig et al., "The use of mucoadhesive polymers in ocular drug delivery," Advanced Drug Delivery Reviews, 57(11): 1595-1639 (2005).
Supplementary European Search Report for EP Application No. 207710955 dated Nov. 28, 2022.

* cited by examiner

*Primary Examiner* — Robert A Wax
*Assistant Examiner* — John W Lippert, III
(74) *Attorney, Agent, or Firm* — Foley Hoag LLP; David P. Halstead

(57) ABSTRACT

The present invention relates to nucleic acid fragment-encapsulated polymer nanoparticles and a method of preparing the same. The polymer may be a mucoadhesive polymer and specifically chitosan, and the nucleic acid fragment may be polydeoxyribonucleotide (PDRN). The nucleic acid fragment-encapsulated polymer nanoparticles may be used as an eye drop. Since the nucleic acid fragment-encapsulated polymer nanoparticles is capable of adhering to the mucus in the eyes, nucleic acid fragments inside the nanoparticles can be slowly released into the ocular mucous membrane. In addition, since nucleic acid fragment-encapsulated polymer nanoparticles can exhibit high efficiency in the eyes even with a small dose of drug, patient convenience can be increased or costs can be reduced.

13 Claims, 13 Drawing Sheets

FIG. 13

| TEST GROUP (CONC.) | NUMBER OF ANIMALS | TOTAL SCORE (MTS) | | | | TOTAL SCORE (MTS) MMTS | EYE IRRITATION ASSESSMENT |
|---|---|---|---|---|---|---|---|
| | | 1 hour | 24 hour | 48 hour | 72 hour | | |
| G1 TEST MATERIAL (100%) | 2 | 0 | 0 | 0 | 0 | 0 | NONIRRITATING |

MMTS : MAXIMUM MEAN TOTAL SCORE
hour : OBSERVATION TIME AFTER APPLICATION
Conc : CONCENTRATION

EYE DROPS CONTAINING CHITOSAN NANOPARTICLES IN WHICH PDRN IS ENCAPSULATED, AND PREPARATION METHOD THEREFOR

RELATED APPLICATIONS

This application is a § 371 national-stage application based on PCT/KR2020/003203, filed on Mar. 6, 2020, which claims priority to Korean Application 10-2019-0027194, filed on Mar. 8, 2019. The entire contents of PCT/KR2020/003203 are incorporated herein by reference in their entirety.

TECHNICAL FIELD

The present invention relates to an eye drop containing chitosan nanoparticles in which polydeoxyribonucleotide (PDRN) is encapsulated and a method of manufacturing the same.

More particularly, the present invention relates to mucoadhesive nanoparticles configured to deliver a drug to the ocular mucous membrane and a method of manufacturing the same, which are capable of increasing the residence time of the drug in the ocular mucous membrane.

BACKGROUND ART

The incidence of eye diseases is increasing with the increase in the elderly population and is increasing in all age groups due to the generalization of digital products such as smartphones and an increase in the use of contact lenses.

Most conventional eye drops used as therapeutic agents for these eye diseases tend to be lost and discharged together with the tear fluid, so there is a problem that only a very small amount actually comes into contact with the cornea. In addition, most of the conventional eye drops do not have long-lasting medicinal effects in the eye, so their bioavailability is quite low.

For this reason, large amounts of drugs are administered for a long period of time or repeatedly for the treatment of eye diseases. However, in this case, there is a problem in that the eyes are easily exposed to the risk of irritation, corneal damage, or infection.

In addition, Korean Laid-Open Patent Application No. 10-2014-0055205 discloses a polydeoxynucleotide eye drop that has long-lasting medicinal effects due to increased viscosity due to the inclusion of a cationic polymer, but there is a disadvantage that since the eye drop has high viscosity, it causes irritation in the eye, so patient discomfort cannot be avoided.

Therefore, there is a need to develop various systems capable of releasing a drug while residing in the mucous membrane for an extended period of time or fundamentally treating the cause of disease by penetrating into cells. In this case, since high bioavailability is possible even with a small amount, drug expenditures and administration frequency can be reduced, and thus patient convenience can be promoted.

DISCLOSURE

Technical Problem

The present invention is directed to providing an eye drop containing chitosan nanoparticles in which PDRN, a bioactive material, is immobilized using chitosan.

The present invention is directed to providing an eye drop containing chitosan nanoparticles capable of delivering PDRN into the mucous membrane and controlling a PDRN release rate.

In addition, the present invention is directed to providing a method of manufacturing eye drops containing chitosan nanoparticles in which PDRN, a bioactive material, is immobilized using adhesive chitosan.

Technical Solution

One aspect of the present invention provides an eye drop in the form of a suspension containing chitosan nanoparticles containing encapsulated PDRN, wherein the chitosan nanoparticles are mucoadhesive, and the chitosan nanoparticles are suspended in any one or more of distilled water, an organic solvent, and a combination thereof.

Another aspect of the present invention provides an eye drop in the form of a suspension containing chitosan nanoparticles containing encapsulated PDRN, which further contains tripolyphosphate (TPP).

Still another aspect of the present invention provides a method of manufacturing an eye drop in the form of a suspension containing PDRN-encapsulated mucoadhesive chitosan nanoparticles, which includes: preparing a chitosan solution by mixing chitosan with water; preparing a PDRN solution by dissolving PDRN in water; preparing a mixed solution by mixing the chitosan solution and the PDRN solution; and performing shearing which disperses the mixed solution at high pressure.

Another aspect of the present invention provides a method for manufacturing an eye drop, wherein the preparation of the PDRN solution further includes the addition of 0.005 to 0.01 g of TPP.

Advantageous Effects

According to the present invention, it is possible to provide an eye drop containing PDRN-encapsulated biodegradable adhesive polymer nanoparticles. Specifically, it is possible to provide chitosan nanoparticles capable of controlling the release rate of encapsulated PDRN.

The eye drop of the present invention can have the effect of releasing a drug while residing in the mucous membrane for an extended period of time due to its long residence time in the eyes or fundamentally treating the cause of the disease by penetrating into cells. In this case, since a high therapeutic effect can be obtained even with a small amount, drug expenditures and administration frequency can be reduced, and thus patient convenience can be promoted.

In addition, the eye drop of the present invention can have a cell-activating effect and can cause less irritation to the ocular mucous membrane.

DESCRIPTION OF DRAWINGS

FIG. 13 shows the results of evaluating the occurrence of irritation of the ocular mucous membrane due to chitosan-PDRN nanoparticles and the level of irritation.

BEST MODE

1. Definition of Terms

Figure 1:
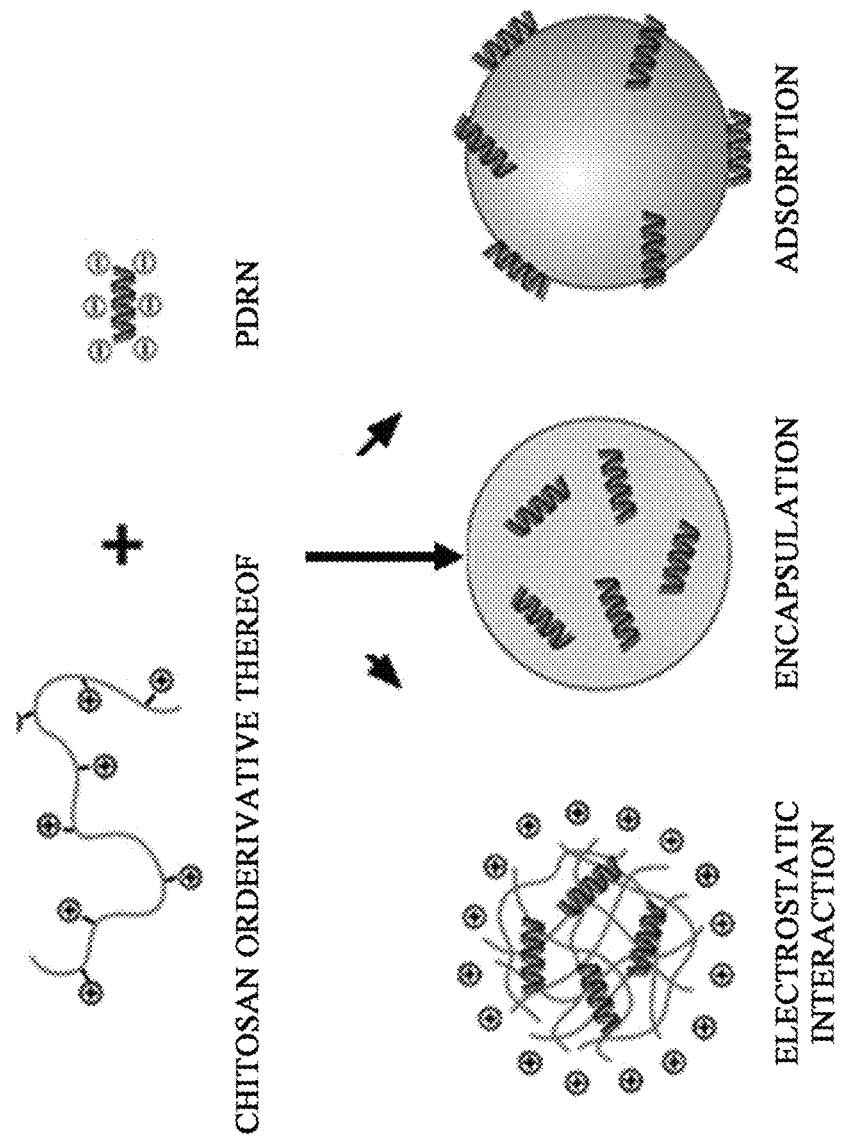
FIG. 1 is an illustration of a PDRN-encapsulated polymer nanoparticle.

The following are definitions of representative terms used in the present specification.

The term "chitosan" refers to a polysaccharide which is a natural polymer obtained by deacetylation (removal of —$CH_3CONH$) of chitin derived from crustacean shells. That is, chitosan is a form in which an acetyl group (—$COCH_3$) present in a monomer of chitin is substituted with an amino group (—$NH_3$). Meanwhile, chitin derived from shells of crustaceans such as crab, crayfish, and shrimp is the second most abundant natural polymer after cellulose, and has a structure in which the OH at the C-2 position of cellulose is substituted with $CH_3CONH$, and is an insoluble material having a structure very similar to that of cellulose.

Chitosan is known as the only cationic material among natural polymers. Chitosan also has an abundance of active amino groups and hydroxyl groups, and the number of active amino groups varies depending on the deacetylation degree of chitin.

Chitosan is biocompatible, nontoxic, has low immunogenicity, and is easily degraded by enzymes. The term "nucleic acid fragment" refers to a deoxyribonucleic acid (DNA) cleavage product, a DNA fragment, or a sheared DNA product.

The term "PDRN" refers to a polydeoxyribonucleotide, which is a mixture of short deoxyribonucleotides. That is, PDRN is a low molecular weight DNA complex formed by fractionating a DNA chain into a certain size. "PDRN" may be a type of the above-described nucleic acid fragment.

The term "encapsulation" means enclosing or coating one material with another material. In one embodiment of the present invention, a chitosan capsule form containing PDRN collected therein may be formed. The term "nanoparticle" refers to a nano-sized particle, and a nanoparticle may contain a specific material therein. In this case, it can be said that the specific material is encapsulated in the nanoparticle. In the present specification, the terms "nanoparticle" and "nanocapsule" may be used interchangeably. The encapsulated specific material can be stably protected from the external environment and released under specific conditions.

The term "mucous membrane" refers to epidermal cells involved in adsorption and secretion that form a membrane surrounding an internal organ or a site exposed to the outside, and examples thereof include, but are not limited to, mucus membranes in the eye, oral cavity, nasal cavity, anus, and vagina.

The term "mucoadhesive polymer" refers to a polymer having the ability to adhere to the mucous membrane. The adhesive polymer may be any one or more of the following: polyisobutylene, sodium polyacrylate, polyacrylate, polybutene, chitosan, and gelatin, but the present invention is not limited thereto.

The term "mucoadhesive polymer nanoparticle" refers to a nanoparticle having an increased residence time in the mucous membrane, and the mucoadhesive polymer nanoparticle may include a material having a mucus-friendly function, and a specific material may be encapsulated inside the nanoparticle.

The term "about" when used with a specific amount, level, value, number, frequency, percentage, dimension, size, quantity, weight, or length means that the referenced amount, level, value, number, frequency, percentage, dimension, size, quantity, weight, or length has a variance of up to 30, 25, 20, 25, 10, 9, 8, 7, 6, 5, 4, 3, 2, or 1%.

In addition to the above terms, other terms will be defined elsewhere in the specification where necessary. Unless explicitly defined otherwise herein, industry terms used in the present specification shall have the meanings recognized in the art.

Here, the present invention will be described in detail.

2. Eye Drop in Form of Suspension

An eye drop of the present invention may be an eye drop in the form of a suspension.

The term "suspension" refers to fine solid particles dispersed and suspended in a liquid. For example, the suspension may refer to nucleic acid fragment-encapsulating polymer nanoparticles dispersed and suspended in a liquid. In another example, the suspension may refer to nucleic acids, nucleic acid fragments, polymers, nucleic acid-encapsulating polymer particles, nucleic acid fragment-encapsulating polymer particles, or a combination thereof dispersed and suspended in a liquid.

The liquid may be distilled water, organic solvent, or a combination thereof, but the present invention is not limited thereto.

Particles included in the suspension may be nanosized.

The size may be 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1,000 nm, or the like, but the present invention is not limited thereto.

The suspension may have a viscosity lower than that of a gel. In other words, the dispersibility of the particles in the suspension is high.

A material may be encapsulated in the particles included in the suspension. The encapsulation efficiency may be 70%, 75%, 80%, 85%, 90%, 95%, 100%, or the like, but the present invention is not limited thereto.

Higher encapsulation efficiencies mean that the particles provide better protection for the material. In other words, the particles are capable of slowly releasing the material. In other words, the half-life of the material is increased.

Advantages of Eye Drops in Form of Suspension

The eye drop may be in the form of a gel, suspension, ointment, or the like. However, eye drops in the form of an ointment or gel may cause various types of discomfort such as blurred vision or stiff eyes. On the other hand, when an eye drop in the form of a suspension is used, the above-described types of discomfort can be reduced compared to when an eye drop in the form of a gel or ointment is used.

Limitations of Eye Drops in Suspension

In general, eye drops in the form of a suspension are only a mixture of materials, and thus, it is difficult for the materials to enter the eyes, and a half-life is short. Therefore, suspension-type eye drops have a limitation of having a shorter residence time than gel- or ointment-type eye drops.

As described above, the present invention relates to an eye drop in the form of a suspension. Therefore, the eye drop of the present invention causes less discomfort than eye drops in the form of a gel or ointment. In particular, to overcome the limitation of a short residence time of conventional suspension-type eye drops, the suspension-type eye drop of the present invention includes an encapsulated material.

When a material is encapsulated, since the material is slowly released, there are advantages in that the material has an increased residence time in the eyes and is not directly exposed to oxygen, light, and the like, and stability is increased because the material does not directly irritate the eyes.

Hereinafter, the eye drop in the form of a suspension containing an encapsulated material will be described in more detail.

The eye drop of the present invention in the form of a suspension includes nucleic acid fragment-encapsulated polymer nanoparticles as a component.

According to one embodiment of the present invention, PDRN-encapsulated chitosan nanoparticles may be provided.

1) PDRN-Encapsulated Polymer Nanoparticles

FIG. 1 is an illustration of a polymer nanoparticle encapsulating PDRN, which is a type of nucleic acid fragment.

According to one embodiment of the present invention, the "nucleic acid fragment-encapsulating polymer nanoparticles" may be in a suspension state.

A. Nanoparticle Components

A-i) Polymer

According to one embodiment of the present invention, the polymer which is one component of the nucleic acid fragment-encapsulated polymer nanoparticles may be an adhesive polymer.

The adhesive polymer is chemically stable and resistant to acids and alkalis. The adhesive polymer is a material used when high viscosity is required, and since it increases adhesion and viscosity and improves the stability of the emulsion, physical properties and tactile properties, it can be mainly used as a thickener, stabilizer, coagulant, wetting agent, or emulsifying and dispersing agent, or for tissue improvement.

For example, the adhesive polymer may be any one or more of polylactide, polyglycolide, poly(lactic-co-glycolic acid), polyorthoester, polyanhydride, polyamino acid, polyhydroxybutyric acid, polycaprolactone, polyalkyl carbonate, ethyl cellulose, chitosan, starch, guar gum, gelatin, collagen, and a salt thereof.

In another example, the adhesive polymer may be any one or more of polyisobutylene, sodium polyacrylate, polyacrylate, polybutene, and a salt thereof.

The adhesive polymer may be a mucoadhesive polymer. The mucous membrane may be any one or more mucous membranes in the eye, oral, nasal, anus, and vagina, but the present invention is not limited thereto.

According to one embodiment of the present invention, the polymer which is one component of the nucleic acid fragment-encapsulated polymer nanoparticles may be a biodegradable polymer.

The term "biodegradable polymer" refers to a polymer that can be chemically degraded after use. Bioabsorbable polymers that undergo molecular weight reduction as chemical bonds are broken in the human body are also examples of biodegradable polymers.

For example, the biodegradable polymer may be gelatin, collagen, fibrin, or elastin, but the present invention is not limited thereto.

In another example, the biodegradable polymer may be alginic acid or hyaluronic acid, but the present invention is not limited thereto.

According to one embodiment of the present invention, the polymer which is one component of the nucleic acid fragment-encapsulated polymer nanoparticles may be any one or more of chitosan, a chitosan derivative, and a chitosan salt.

The chitosan salt may be chitosan hydrochloride (hereinafter referred to as CHC), but the present invention is not limited thereto.

The chitosan derivative may be an alkylate, acylate, arylate, sulfate, or phosphate of chitosan, but the present invention is not limited thereto.

One or more of the chitosan, chitosan derivative, and chitosan salt may be water-soluble or water-insoluble.

For example, any one or more of the chitosan, chitosan derivative, and chitosan salt may be soluble in water.

In another example, any one or more of the chitosan, chitosan derivative, and chitosan salt may be soluble in an organic acid. Specifically, any one or more of the chitosan, the chitosan derivative, and chitosan salt may be soluble in formic acid, lactic acid, ascorbic acid, or acetic acid, but the present invention is not limited thereto.

In another example, any one or more of the chitosan, chitosan derivative, and chitosan salt may be soluble in an inorganic acid. Specifically, any one or more of the chitosan, chitosan derivative, and chitosan salt may be soluble in diluted hydrochloric acid, but the present invention is not limited thereto.

There may be no restriction on the molecular weight of chitosan, chitosan derivative, and chitosan salt.

For example, the molecular weight of the chitosan, chitosan derivative, and chitosan salt may be in the range of 300 to 6,000, 6,000 to 12,000, 12,000 to 150,000, or 150,000 to 800,000 [g/mol], but the present invention is not limited thereto.

Chitosan may be deacetylated chitin.

For example, the degree of deacetylation (DD) of chitin to chitosan may be 100%.

In another example, the DD of chitin to chitosan may be in the range of 95% to 100%.

In another example, the DD of chitin to chitosan may be in the range of 85% to 95%.

In yet another example, the DD of chitin to chitosan may be in the range of 75% to 85%.

In yet another example, the DD of chitin to chitosan may be in the range of 65% to 75%.

In yet another example, the DD of chitin to chitosan may be in the range of 55% to 65%.

In yet another example, the DD of chitin to chitosan may be 55% or less.

A-ii) Nucleic Acid Fragments

According to one embodiment of the present invention, nucleic acid fragments which are one component of the nucleic acid fragment-encapsulated polymer nanoparticles may be DNA fragments or ribonucleic acid (RNA) fragments. That is, the nucleic acid fragments may be double-stranded nucleic acid fragments or single-stranded nucleic acid fragments.

The term "nucleic acid fragment" may refer to a biopolymer formed of phosphoric acid, four types of bases, and deoxyribose or ribose, which is in the form of a fragment with reduced molecular weight.

The nucleic acid fragment may be a DNA fragment having 10 to 1,000 bases or base pairs, but the present invention is not limited thereto.

The nucleic acid fragment may be a RNA fragment having 10 to 1,000 bases or base pairs, but the present invention is not limited thereto.

For example, a nucleic acid fragment may be a DNA fragment or an RNA fragment having 10 to 50 bases or base pairs.

In another example, the nucleic acid fragment may be a DNA fragment or RNA fragment having 50 to 800 bases or base pairs. Specifically, the nucleic acid fragment may be a DNA fragment or RNA fragment that has 50 to 750 bases or base pairs.

In another example, the nucleic acid fragment may be a DNA fragment or RNA fragment having 800 to 1,000 bases or base pairs.

The nucleic acid fragment may be a polydeoxyribonucleotide (hereinafter referred to as PDRN).

PDRN may be a combination of the DNA and/or RNA fragments described above.

The PDRN may be derived from a living organism.

For example, PDRN may be derived from any one or more of a fish, an animal, or a plant. Specifically, the PDRN may be derived from fish sperm, semen, and/or testis.

The fish may be a species in the order Salmoniformes and/or the family Salmonidae. For example, the fish may be a species in the genus Oncorhynchus or the genus *Salmo*.

The PDRN may have 10 to 1,000 bases or base pairs, but the present invention is not limited thereto.

For example, the PDRN may have 10 to 50 bases or base pairs.

In another example, the PDRN may have 50 to 800 bases or base pairs. Specifically, the PDRN may have 50 to 750 bases or base pairs.

In another example, the PDRN may have 800 to 1,000 bases or base pairs.

A-iii) Additional Components

According to one embodiment of the present invention, tripolyphosphate (TPP) may be added as an additional component of the nucleic acid fragment-encapsulated polymer nanoparticles. The TPP can be referred to as sodium triphosphate (STP), sodium tripolyphosphate (STPP), or $Na_5P_3O_{10}$.

When TPP is added as an additional component of the nucleic acid fragment-encapsulated polymer nanoparticles, since nucleic acid fragments can exhibit ionicity, there is an advantage that even large nucleic acid fragments can be easily encapsulated in the nanoparticles.

B. Characteristics of Nanoparticles

B-i) Size of Nanoparticles

According to one embodiment of the present invention, the diameter of nucleic acid fragment-encapsulated polymer nanoparticles may be in the range of 100 nm to 1,000 nm.

For example, nucleic acid fragment-encapsulated polymer nanoparticles may have a diameter of 100 nm to 200 nm.

In another example, nucleic acid fragment-encapsulated polymer nanoparticles may have a diameter of 200 nm to 400 nm.

In still another example, the nucleic acid fragment-encapsulated polymer nanoparticles may have a diameter of 400 nm to 600 nm.

In yet another example, the nucleic acid fragment-encapsulated polymer nanoparticles may have a diameter of 600 nm to 800 nm.

In yet another example, the nucleic acid fragment-encapsulated polymer nanoparticles may have a diameter of 800 nm to 1,000 nm.

B-ii) PDRN Protection by Nanoparticles

According to one embodiment of the present invention, in the nucleic acid fragment-encapsulated polymer nanoparticles, the nucleic acid fragments may be protected from an enzyme or the external environment. The enzyme may be a deoxyribonuclease (DNase) or a ribonuclease (RNase), but the present invention is not limited thereto.

That is, the nucleic acid fragment-encapsulated polymer nanoparticles of the present invention are a type of material capable of preventing the nucleic acid fragments from being degraded by a DNase or an RNase.

C. PDRN-Encapsulated Polymer Nanoparticle Preparation Method

According to one embodiment of the present invention, a method of preparing nucleic acid fragment-encapsulated polymer nanoparticles may be provided.

According to one embodiment of the present invention, a method for preparing PDRN-encapsulated polymer nanoparticles may be provided.

According to one embodiment of the present invention, a method of preparing PDRN-encapsulated chitosan nanoparticles may be provided.

According to one embodiment of the present invention, the "nucleic acid fragment-encapsulated polymer nanoparticles" may be prepared in a suspension state.

According to some embodiments of the present invention, the nucleic acid fragment-encapsulated polymer nanoparticles may be prepared by an ionic gelation method or a coacervation method.

According to some embodiments of the present invention, the nucleic acid fragment-encapsulated polymer nanoparticles may be prepared by a solvent evaporation method, an instant emulsion method, and a solvent dispersion method, but the present invention is not limited thereto.

According to some embodiments of the present invention, the nucleic acid fragment-encapsulated polymer nanoparticles may be prepared by a supercritical liquid technique, particle replication in nonwetting templates, and self-assembly and electrospinning methods, but the present invention is not limited thereto.

For example, a method for preparing nucleic acid fragment-encapsulated mucoadhesive chitosan nanoparticles may include:
  i) preparing a chitosan solution by mixing chitosan with water;
  ii) preparing a nucleic acid fragment solution by dissolving nucleic acid fragments in water;
  iii) preparing a mixed solution by mixing the chitosan solution and the nucleic acid fragment solution; and
  iv) performing shearing that disperses the mixed solution at high pressure.

The term "shearing" may refer to a processing method in which a shear force is applied to a component to break it into fragments of a desired size or shape. The shearing may break the component into fragments using a shearing force generated from any one or more of the pressure and flow rates, but the present invention is not limited thereto.

According to some embodiments of the present invention, shearing may result in polymer nanoparticles in which nucleic acid fragments of various sizes are encapsulated.

Specifically, a method of preparing PDRN-encapsulated mucoadhesive chitosan nanoparticles may include:
i) prepare a chitosan solution by mixing chitosan with water;
ii) preparation of a PDRN solution by dissolving PDRN in water;
iii) prepare a mixed solution by mixing the chitosan solution and the PDRN solution; and
iv) perform shearing that disperses the mixed solution at high pressure.

The above-described steps of preparing a chitosan solution, preparing a nucleic acid fragment solution (e.g., PDRN solution), and preparing a mixed solution may be carried out at room temperature conditions.

The step of preparing a nucleic acid fragment solution (e.g., PDRN solution) may also include the addition of TPP.

For example, the step of preparing a nucleic acid fragment solution (e.g., PDRN solution) may further include adding 0.005 to 0.01 g of TPP.

In another example, the step of preparing a nucleic acid fragment solution (e.g., PDRN solution) may also include adding 0.01 to 0.05 g of TPP.

In still another example, the step of preparing a nucleic acid fragment solution (e.g., PDRN solution) may further include adding 0.05 to 0.1 g of TPP.

The shearing may be performed using any one or more of a high-pressure homogenizer, a high-pressure disperser, an ultrahigh-pressure homogenizer, and an ultrahigh-pressure disperser, but the present invention is not limited thereto.

In the shearing, the mixed solution may be dispersed in an aqueous solution under various pressures, flow rates, and temperatures, resulting in nucleic acid fragment (e.g., PDRN)-encapsulated polymer nanoparticles, but the present invention is not limited thereto.

Shearing may be performed under a pressure condition of 10,000 to 50,000 psi, but the present invention is not limited thereto.

For example, shearing can be performed under a pressure condition of 10,000 to 20,000 psi. In another example, the shearing may be performed under a pressure condition of 20,000 to 50,000 psi.

The shearing may be performed under a flow rate condition of 50 to 150 ml/min, but the present invention is not limited thereto.

For example, shearing can be performed under a flow rate condition of 50 to 80 ml/min. In another example, the shearing may be performed under a flow rate condition of 80 to 120 ml/min. In still another example, the shearing may be performed under a flow rate condition of 120 to 150 ml/min.

Shearing may be performed under a temperature condition of 0 to 15° C., but the present invention is not limited thereto.

For example, the shearing may be performed under a temperature condition of 2 to 6° C. In another example, the shearing may be performed under a temperature condition of 6 to 10° C. In still another example, the shearing may be performed under a temperature condition of 10 to 15° C.

The shearing may be performed once, or repeated two or more times.

For example, the shearing may be performed once or repeated 2 to 5 times, 5 to 10 times, 10 to 15 times, or 15 to 20 times, but the present invention is not limited thereto.

3. Eye Drop Containing PDRN-Encapsulated Polymer Nanoparticles

According to one embodiment of the present invention, a pharmaceutical composition containing nucleic acid fragment-encapsulated polymer nanoparticles may be provided.

The pharmaceutical composition may be made up of components approved as pharmaceutical raw materials as designated by the Food and Drug Administration and may be prepared by a conventional method used by those of ordinary skill in the art.

The pharmaceutical composition may be a solid preparation for internal use, an injection, an eye drop, a liquid preparation for internal use, a liquid preparation for external use, an ointment, a patch, a solid preparation, or a liquid preparation, but the present invention is not limited thereto.

The liquid preparation for external use may be intended for the purpose of systemic and local administration and treatment. The liquid preparation for external use may be any one or more of an ointment, a gel, a sublingual drug, an oral tablet, a syrup, a spray for the oral cavity and the lower respiratory tract, an aspiration agent, a suspension agent, a POP preparation, and a patch. The liquid preparation for external use may be a lotion, a liniment, an aerosol, an aerosol for external use, a pump spray, an enema, a gargle, a hemodialysis solution, a dialysis solution, an ear drop, a nasal drop, an eye drop, or a nasal solution, but the present invention is not limited thereto.

The injection may be any one or more of an intravenous injection, a subcutaneous injection, and an intramuscular injection, but the present invention is not limited thereto. The injection may be a powder injection, an infusion, a freeze-dried injection, an implant, a long-acting injection, a peritoneal dialysis agent, a perfusion, or a dialysis agent, but the present invention is not limited thereto.

Base materials or additives used for the preparation of the above-described liquid preparation for external use or injection may include ingredients generally used in the art.

According to one embodiment of the present invention, an eye drop containing nucleic acid fragment-encapsulated polymer nanoparticles may be provided. In this case, the eye drop may be an eye drop in the form of a suspension.

According to one embodiment of the present invention, an eye drop containing PDRN-encapsulated polymer nanoparticles may be provided. In this case, the eye drop may be an eye drop in the form of a suspension.

According to one embodiment of the present invention, an eye drop containing PDRN-encapsulated chitosan nanoparticles may be provided. In this case, the eye drop may be an eye drop in the form of a suspension.

4. Effects of Eye Drop in Form of Suspension Containing PDRN-Encapsulated Polymer Nanoparticles 4-1. Effect Upon Instillation in the Eye Compared to gel-type eye drops that are only a mixture of nucleic acid fragments and polymers, an eye drop in the form of a suspension containing nucleic acid fragment-encapsulated polymer nanoparticles has the advantage of causing less discomfort in the eye when instilled into the eye.

Specifically, when a gel-type eye drop is used, various types of discomfort, such as blurred vision or stiff eyes, may occur; but in the case of an eye drop containing nucleic acid fragment-encapsulated polymer nanoparticles, since the eye drop is not in the form of a gel and is in a suspension state in which the nanoparticles are dispersed, the above types of discomfort can be reduced.

That is, using an eye drop composition in the form of a gel in which an adhesive polymer is mixed with nucleic acid fragments may be less desirable than using an eye drop containing nucleic acid fragment-encapsulated polymer nanoparticles in terms of cost and comfort.

Because of the discomfort, it is evident in the art that eye drops that are not in gel form are preferentially prescribed, and when it is difficult to treat with the eye drops, eye drops in gel form are sub optimally prescribed.

4-2. Effects in Eye

Compared with eye drops containing nucleic acid fragments, eye drops containing nucleic acid fragment-encapsulated polymer nanoparticles may have a longer residence time in the eyes. This may be because the polymer nanoparticles protect the nucleic acid fragments from enzymes or various conditions in the living body or because the nucleic acid fragment-encapsulated polymer nanoparticles adhere to the mucous membrane of the eye, they can reach the eyes better than eye drops simply containing nucleic acid fragments.

For example, the half-life of the eye drop containing nucleic acid fragment-encapsulated polymer nanoparticles may be about two to three times the half-life of the eye drops containing nucleic acid fragments.

In another example, the half-life of the eye drop containing nucleic acid fragment-encapsulated polymer nanoparticles may be about three to four times the half-life of eye drops containing nucleic acid fragments.

In another example, the half-life of the eye drop containing nucleic acid fragment-encapsulated polymer nanoparticles may be about four to five times the half-life of the eye drops containing nucleic acid fragments.

In yet another example, the half-life of the eye drop containing nucleic acid fragment-encapsulated polymer nanoparticles may be about five to six times the half-life of eye drops containing nucleic acid fragments.

In addition, when the eye drop containing nucleic acid fragment-encapsulated polymer nanoparticles is instilled in the eyes, cells in the eyes can be activated.

For example, when an eye drop containing nucleic acid fragment-encapsulated polymer nanoparticles is treated at a concentration of 150 to 200 μg/ml per volume of eye drop, cell viability may be approximately 1.2 times higher than when the eye drop is not treated.

In another example, when an eye drop containing nucleic acid fragment-encapsulated polymer nanoparticles is treated at a concentration of 200 to 300 μg/ml per eye drop volume, cell viability may be approximately 1.3 times higher than when the eye drop is not treated.

In still another example, when an eye drop containing nucleic acid fragment-encapsulated polymer nanoparticles at a concentration of 300 to 400 μg/ml per eye drop volume is treated, cell viability may be about 1.5 times higher than when the eye drop is not treated.

Modes of Invention

Hereinafter, the effects of the nucleic acid fragment-encapsulated polymer nanoparticles provided in the present invention will be described in more detail through exemplary embodiments.

The present inventors prepared i) PDRN-encapsulated chitosan nanoparticles and ii) PDRN-encapsulated chitosan nanoparticles containing TPP and evaluated properties thereof.

In addition, the present inventors evaluated the physicochemical properties of the nanoparticles and evaluated the effects and safety of the nanoparticles.

For convenience of explanation, hereinafter, the PDRN-encapsulated chitosan nanoparticles will be referred to as "Chitosan-PDRN nanoparticles," and the PDRN-encapsulated chitosan nanoparticles containing TPP will be referred to as "Chitosan-PDRN-TPP nanoparticles."

[Experimental Example 1] Preparation of Chitosan-PDRN Nanoparticles

The present inventors prepared chitosan-PDRN nanoparticles in a suspension state by mixing a first chitosan solution and a first PDRN solution.

Hereinafter, a method of preparing the first chitosan solution will be described.

0.8 g of CHC was added to 80 ml of distilled water and stirred overnight until completely dissolved. Subsequently, distilled water was added until the mixed solution reached 100 ml. Impurities were removed from the mixed solution using a 0.45 μm filter, and the mixed solution from which impurities were removed was kept for 30 minutes at room temperature (first chitosan solution).

Hereinafter, a method for preparing the first PDRN solution will be described.

160 mg of PDRN was added to 100 ml of water and the mixed solution was stirred at room temperature for two hours. The mixed solution was then filtered through a 0.45 μm filter, and the filtered mixed solution was maintained for 30 minutes at room temperature (first PDRN solution).

Subsequently, the first PDRN solution was added dropwise to the first chitosan solution at room temperature while slowly stirring. After the dropwise addition of the first PDRN solution was completed, the resulting mixture was stirred for 30 minutes at room temperature.

Hereinafter, the mixed solution of the first chitosan solution and the first PDRN solution subjected to the above-described processes will be referred to as "first chitosan-first PDRN solution."

The first chitosan-first PDRN solution was sheared using a high-pressure disperser (Microfluidics M-110EH-30).

Shearing was carried out under the conditions of a pressure of 20,000 psi, a chamber temperature of 5 to 8° C., and a flow rate of 80 to 120 ml/min. The shearing was repeated five times under the same conditions.

The first sheared chitosan-first PDRN solution was filtered under reduced pressure using a 1 μm filter, and finally a colorless liquid was obtained. The colorless liquid was Chitosan-PDRN nanoparticles in a suspension state.

Figure 2:
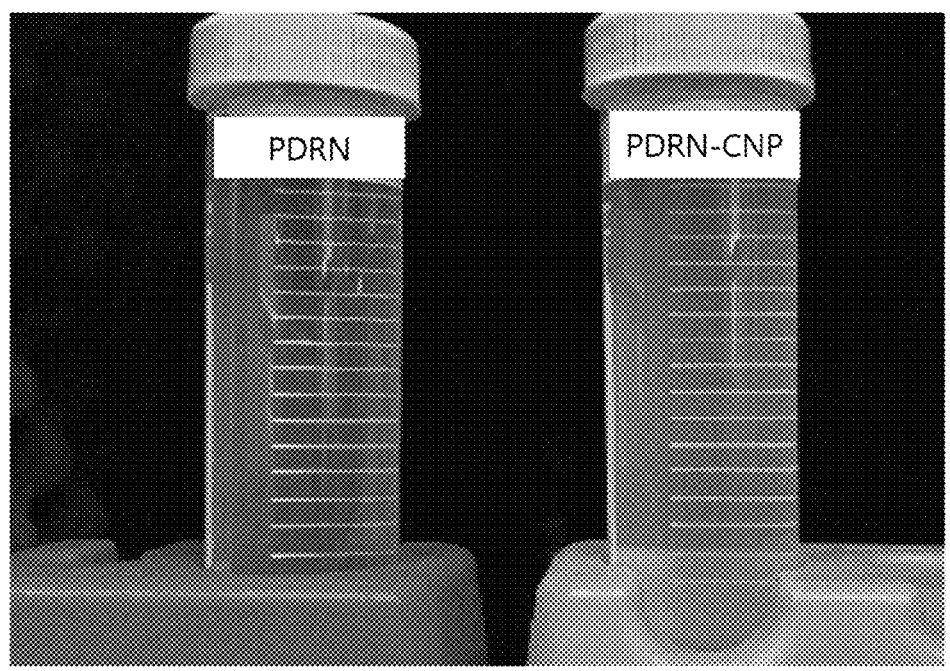
FIG. 2 shows chitosan-PDRN nanoparticles in a suspension state.

FIG. 2 shows the chitosan-PDRN nanoparticles in a suspension state.

To measure the encapsulation efficiency of PDRN, the amount of PDRN added and the amount of PDRN remaining in a suspension containing chitosan-PDRN nanoparticles were measured, and the encapsulation efficiency of PDRN was calculated according to the following equation. The encapsulation efficiency of PDRN in the nanoparticles prepared in Experimental Example 1 was 95%.

Encapsulation efficiency (EF) (%)={Total addition amount of PDRN (Total PDRN)−Amount of PDRN remaining in suspension (Free PDRN)}× 100%

[Experimental Example 2] Preparation of Chitosan-PDRN-TPP Nanoparticles

The present inventors prepared chitosan-PDRN-TPP nanoparticles in a suspension state by mixing a second chitosan solution and a second PDRN solution.

Hereinafter, a method of preparing the second chitosan solution will be described.

0.4 g of CHC was added to 80 ml of distilled water and stirred overnight until completely dissolved. Subsequently, distilled water was added until the mixed solution reached 100 ml. Impurities were removed from the mixed solution using a 0.45 μm filter, and the mixed solution from which impurities were removed was kept for 30 minutes at room temperature (second chitosan solution).

Hereinafter, a method for preparing the second PDRN solution will be described.

PDRN was added to 100 ml of water and the mixed solution was stirred at room temperature for two hours. The concentration of PDRN in the mixed solution was adjusted to 800 m/ml, and 0.01 g of TPP was added.

The mixed solution to which TPP was added was filtered through a 0.45 μm filter, and the filtered mixed solution was maintained for 30 minutes at room temperature (second PDRN solution).

Subsequently, the second PDRN solution was added dropwise to the second chitosan solution at room temperature while slowly stirring. After the dropwise addition of the second PDRN solution was completed, the resultant was stirred for 30 minutes at room temperature.

100 ml of 0.98 M NaCl was added to the mixed solution of the second chitosan solution and the second PDRN solution, and as 2 M NaOH was added dropwise, the mixed solution of the second chitosan solution and the second PDRN solution was neutralized to pH 7. Subsequently, the neutralized mixed solution of the second chitosan solution and the second PDRN solution was centrifuged at 4,000 rpm for 20 minutes and the supernatant was removed. 70 ml of distilled water was added to the mixed solution from which the supernatant was removed and stirred for 30 minutes.

Hereinafter, the mixed solution of the second chitosan solution and the second PDRN solution subjected to the above-described processes will be referred to as "second chitosan-second PDRN solution."

The second chitosan-second PDRN solution was sheared using a high-pressure disperser (Microfluidics M-110EH-30).

Shearing was carried out under the conditions of a pressure of 20,000 psi, a chamber temperature of 5 to 8° C., and a flow rate of 80 to 120 ml/min. The shearing was repeated five times under the same conditions.

The sheared second chitosan-second PDRN solution was filtered under reduced pressure using a 1 μm filter, and finally, a colorless liquid was obtained. The colorless liquid was Chitosan-PDRN-TPP nanoparticles in a suspension state.

Encapsulation was confirmed by measuring the particle size of the obtained solution and the excess nucleic acid fragments present in the filtrate using a nanoparticle size analyzer (Zetasizer).

The encapsulation efficiency of PDRN in the nanoparticles prepared in Experimental Example 2 was 95%.

[Experimental Example 3] Characterization of Nanoparticles 3-1. Measurement of Nanoparticle Size The present inventors measured the size of the nanoparticles of Experimental Examples 1 and 2 using an SEM (SEISS, Germany).

For the measurement of nanoparticle size, the products of Experimental Examples 1 and 2 were dripped onto glass plates, and moisture was evaporated with warm air. After repeating the same procedure two more times, the size of the particles was measured at 20,000× magnification through an SEM.

As a result, it was found that the nanoparticles had a diameter (size) distribution of 160 nm to 1,000 nm.

Figure 3:
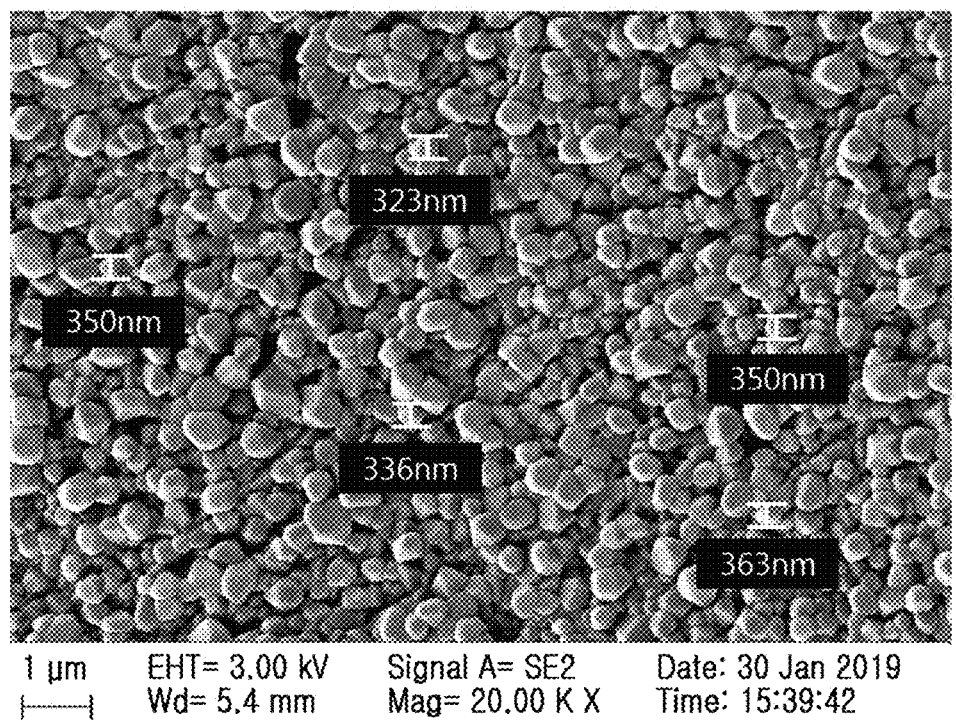
FIG. 3 shows chitosan-PDRN nanoparticles and the size of the nanoparticles confirmed using a scanning electron microscope (SEM).

FIG. 3 shows Chitosan-PDRN nanoparticles and the size of the nanoparticles confirmed using an SEM.

Figure 4:
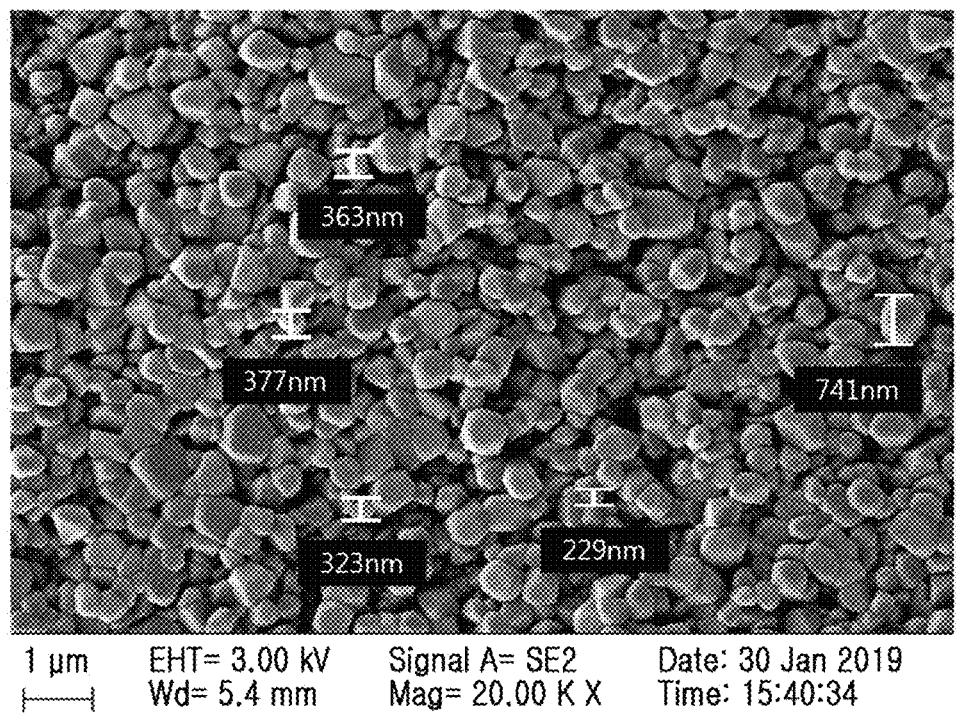
FIG. 4 shows chitosan-PDRN-TPP nanoparticles and the size of the nanoparticles confirmed using an SEM.

FIG. 4 shows the Chitosan-PDRN-TPP nanoparticles and the size of the nanoparticles confirmed by SEM.

3-2. Nanoparticle Distribution and Electric Potential Measurement

The nanoparticle distribution and electric potential of the suspensions obtained in Experimental Examples 1 and 2 were measured using a dynamic light scattering device (Zetasizer) (Malvern Instruments, UK).

1 mL of the suspensions of Experimental Examples 1 and 2 was placed in a cuvette and the intensity of the scattering was measured at 25° C. for 70 seconds at a distance of 3 m.

It was found that Chitosan-PDRN nanoparticles had a diameter (size) distribution of 161 to 925 nm and an average particle diameter (size) of 366.42 nm.

It was found that Chitosan-PDRN-TPP nanoparticles had a diameter (size) distribution of 141 to 1,066 nm and an average particle diameter (size) of 351.24 nm.

Figure 5:
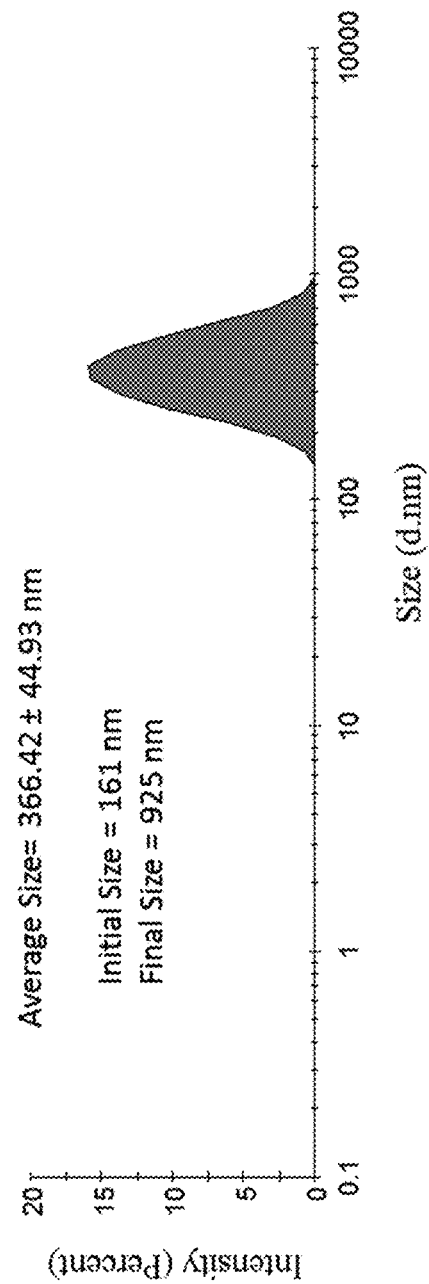
FIG. 5 shows the size distribution and average particle size of chitosan-PDRN nanoparticles.

FIG. 5 shows the size distribution and average particle size of the Chitosan-PDRN nanoparticles.

Figure 6:
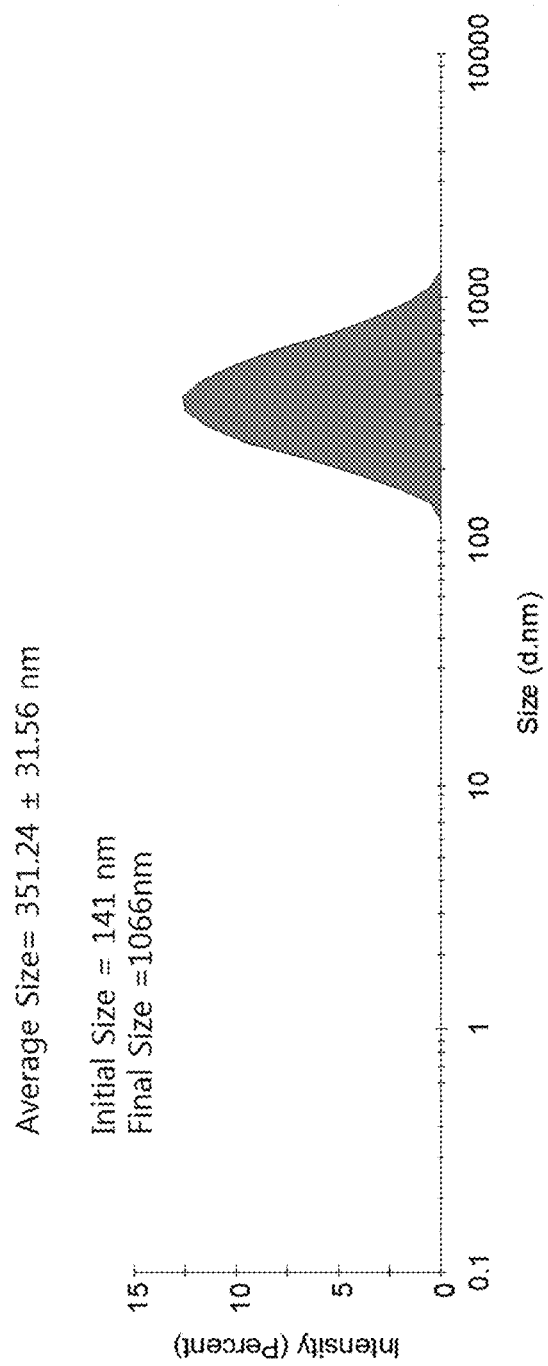
FIG. 6 shows the size distribution and average particle size of chitosan-PDRN-TPP nanoparticles.

FIG. 6 shows the size distribution and average particle size of Chitosan-PDRN-TPP nanoparticles.

In addition, the zeta potential in a double layer was measured under the same conditions.

chitosan-PDRN nanoparticles were found to have a zeta potential range of 16.2 to 54.9 mV and an average zeta potential of 38.52 mV.

It was found that Chitosan-PDRN-TPP nanoparticles had a zeta potential range of 28.3 to 55.7 mV and an average zeta potential of 43.52 mV.

Figure 7:
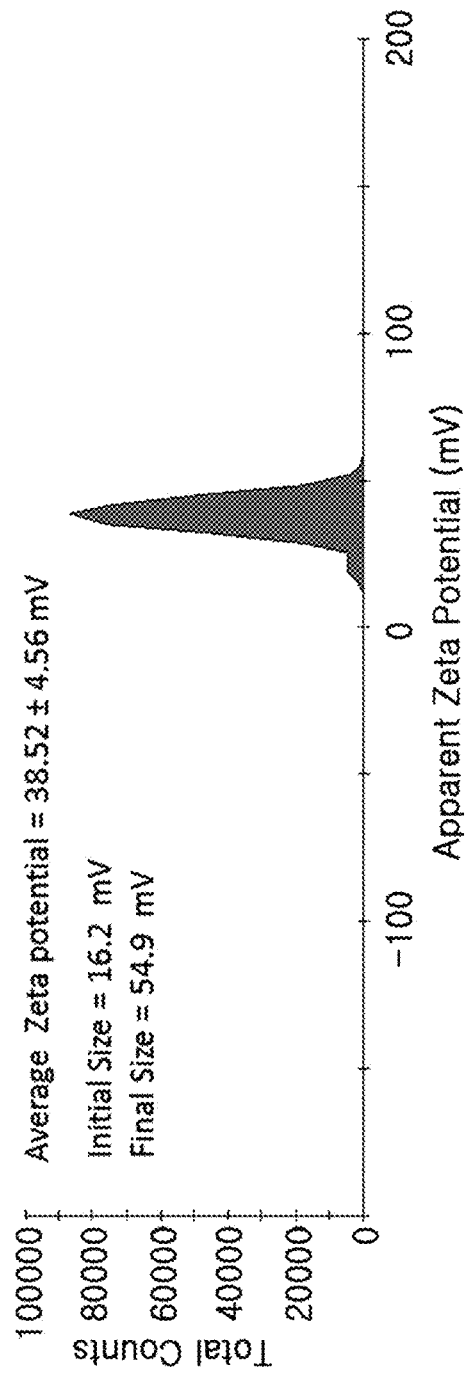
FIG. 7 shows the zeta potential distribution and average zeta potential of chitosan-PDRN nanoparticles.

FIG. 7 shows the zeta potential distribution and average zeta potential of Chitosan-PDRN nanoparticles.

Figure 8:
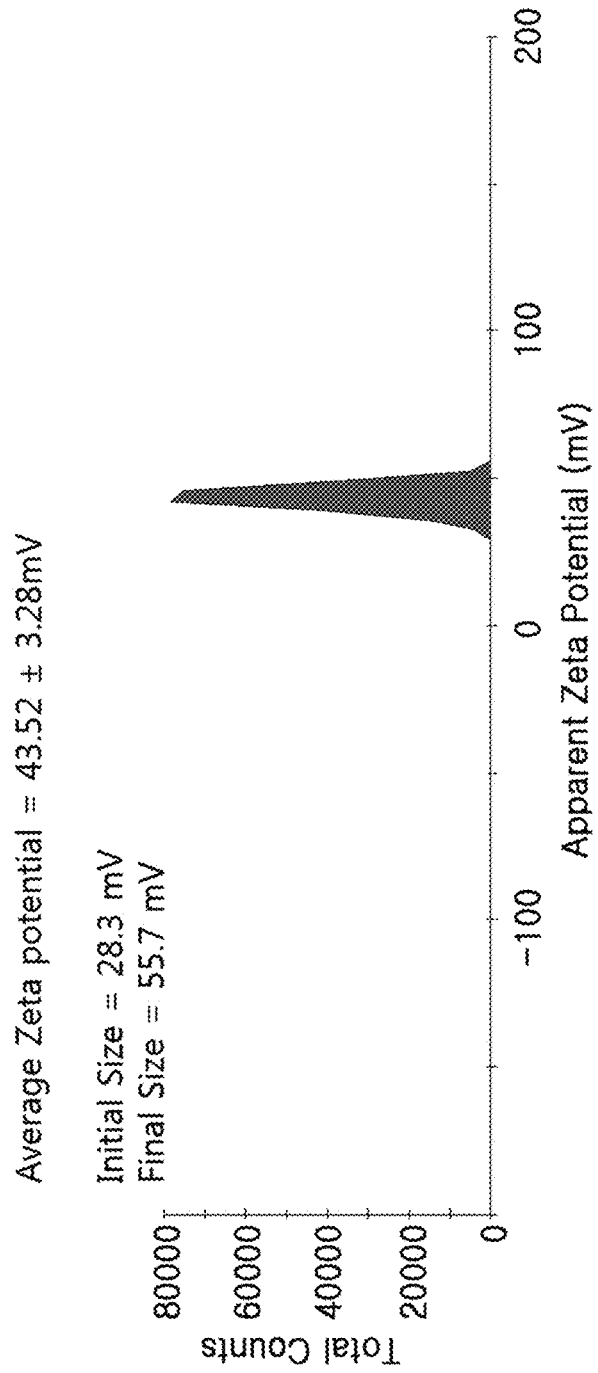
FIG. 8 shows the zeta potential distribution and average zeta potential of chitosan-PDRN-TPP nanoparticles.

FIG. 8 shows the zeta potential distribution and average zeta potential of Chitosan-PDRN-TPP nanoparticles.

It was confirmed that the average zeta potential of Chitosan-PDRN-TPP nanoparticles was higher than the average zeta potential of Chitosan-PDRN nanoparticles. It can be seen that when TPP is added, since the nucleic acid fragment can exhibit ionicity, the electric current can flow relatively well and the zeta potential is high.

3-3. XRD Analysis of the Chitosan Component of Nanoparticles

The present inventors analyzed the chitosan used for encapsulation and PDRN-encapsulated chitosan (Chitosan-PDRN nanoparticles) through XRD using Ultima IV (Rigaku) under the conditions of 40 kV and 40 mA. As a result, it was found that chitosan crystals before and after a reaction were different (see FIG. 9, upper (red) line: chitosan, lower (blue) line: Chitosan-PDRN nanoparticles).

Figure 9:
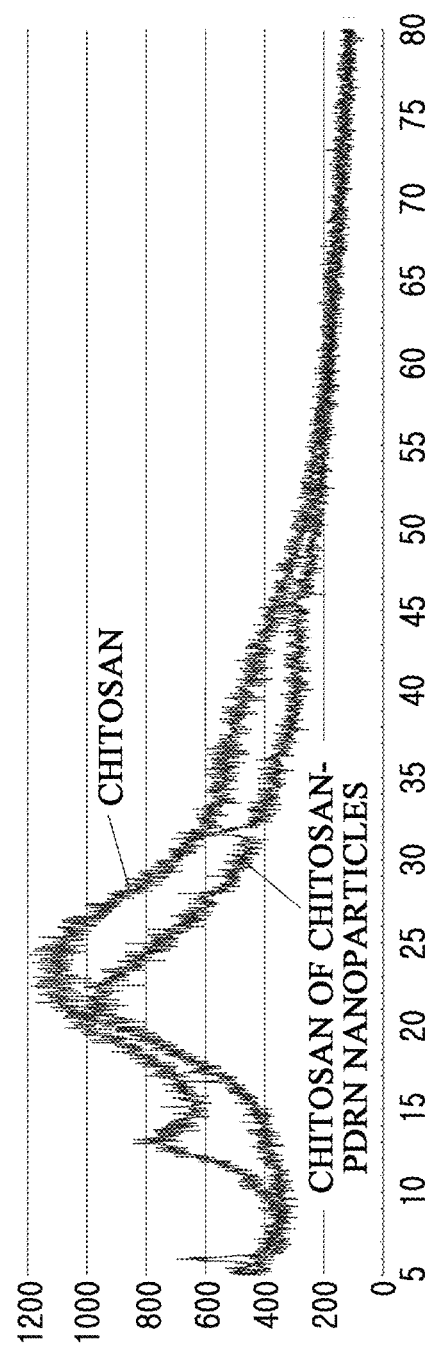
FIG. 9 shows the results of analyzing chitosan used for encapsulation and PDRN-encapsulated chitosan through X-ray diffraction (XRD).

FIG. 9 shows the results of the analysis of the chitosan used for encapsulation and the PDRN-encapsulated chitosan by XRD.

As a result of the XRD analysis of chitosan and PDRN-encapsulated chitosan, it was found that the peak positions were different. Through this, it can be seen that the crystals of PDRN-encapsulated chitosan and chitosan are different.

3-4. Confirmation of the Presence of PDRN in Nanoparticles

The encapsulation of PDRN in chitosan nanoparticles and the content of PDRN were confirmed through electrophoresis.

Figure 10:
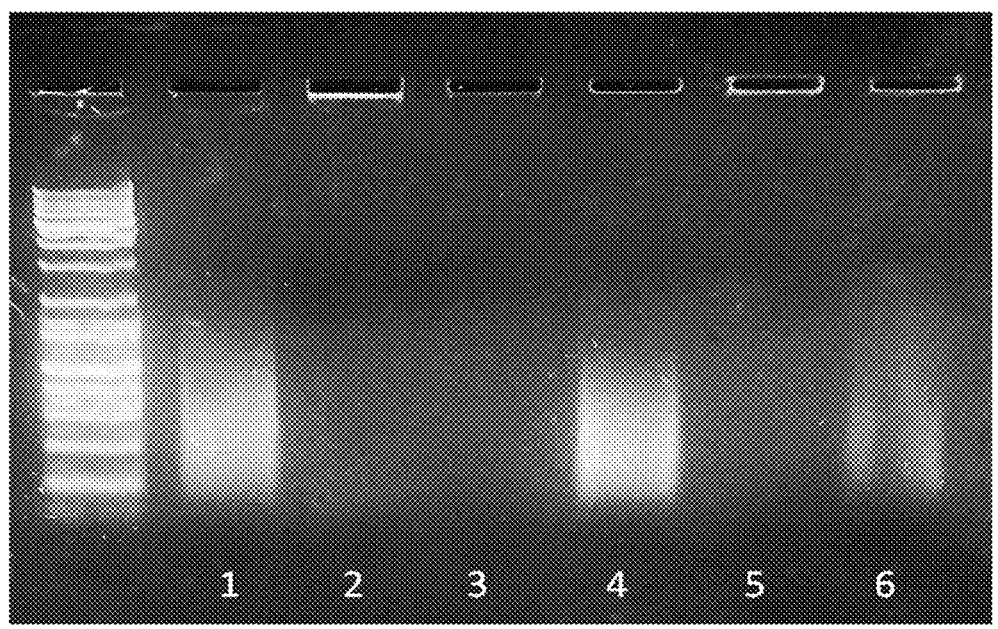
FIG. 10 shows the results of confirming the presence of PDRN in chitosan-PDRN nanoparticles through electrophoresis.

FIG. 10 shows the results of confirming the presence of PDRN in chitosan-PDRN nanoparticles by electrophoresis. In lanes 1 to 6 of FIG. 10, a PDRN solution, a Chitosan-PDRN nanoparticle suspension, a solution containing PDRN treated with DNase, a solution containing Chitosan-PDRN nanoparticles treated with a chitosan-degrading enzyme (hereinafter referred to as chitosanase), a solution containing Chitosan-PDRN nanoparticles treated with DNase, and a solution in which a solution containing chitosan-PDRN nanoparticles treated with DNase-treated Chitosan-PDRN nanoparticles was treated with a solution containing chitosanase were loaded, respectively.

1.5 μL of a DNA degradation enzyme (hereinafter referred to as DNase) solution (Sigma, EN0771) was added to 20 μl of the suspension of Experimental Example 1 and the total volume was increased to 100 μl using a DNase buffer. The present inventors reacted the solution, to which DNase was added, in an incubator at 37° C. for 30 minutes while shaking.

Subsequently, it was confirmed, through electrophoresis, that the suspension of Experimental Example 1 was not affected by the DNA-degrading enzyme (see line 5 of FIG. 10). Also, it was confirmed that PDRN in a control was completely broken down by a DNase (see lanes 1 and 3 of FIG. 10). Through this, the present inventors confirmed that when PDRN is encapsulated by chitosan nanoparticles, PDRN can be protected from a DNA-degrading enzyme.

In addition, 5 μL of chitosanase was added to 20 μl of the suspension of Experimental Example 1. The present inventors reacted to the solution, to which chitosanase was added, in an incubator at 65° C. for 10 minutes.

Subsequently, it was confirmed, by electrophoresis, that the material of Experimental Example 1 appeared at the droplet position (see lane 2 of FIG. 10), but the material of Experimental Example 1 treated with chitosanase was moved to the same position as PDRN (see lane 4 of FIG. 10), and through this, it was confirmed that PDRN was loaded inside the chitosan nanoparticles.

After adding 1.5 μl of a DNase to 20 μl of the suspension of Experimental Example 1 in the same manner as described above, 5 μl of chitosanase was added and incubation was carried out at 65° C. for 10 minutes. As a result of performing electrophoresis using the incubated solution, it was confirmed that the solution was moved to a position corresponding to PDRN (see lanes 1 and 6 of FIG. 10).

[Experimental Example 4] Evaluation of Efficacy and Safety of Nanoparticles 4-1. Evaluation of Residence Time of Nanoparticles in Eyes For in vivo evaluation of PDRN-encapsulated chitosan nanoparticles, 2.1 to 2.2 kg 11-week-old male New Zealand White Rabbits without eye health issues were used. The rabbits were housed one by one in regular cages in a temperature-controlled room, and were allowed to freely ingest water and feed on a light-dark cycle of 12 hours.

After pulling the eyelids under the rabbits' eyes (i.e., lower eyelids of the rabbits) away from the eyes, forming a cup-like shape, the present inventors instilled 0.5 ml of each of the material (1.2 mg/ml) prepared in Experimental Example 1 and a control material (PDRN, 1.2 mg/ml) of the same concentration into the conjunctival sac. PDRN, which is the control material, and the material prepared in Experimental Example 1 were instilled once into the left eye and the right eye, respectively, using a 1 ml syringe. To prevent loss of the instilled materials, the present inventors kept the eyes closed for about 10 seconds after instillation.

Rabbit tears were collected for three seconds using a gauze and collected at each of one minute, three minutes, five minutes, 10 minutes, 20 minutes, 30 minutes, 60 minutes, and 120 minutes after administration.

Each gauze containing the collected rabbit tears was placed in distilled water and centrifuged to collect tears. Drug concentrations in the collected tears were measured over time using a Genova Nano microvolume spectrophotometer (Jenway).

It was found that the half-life of the material prepared in Experimental Example 1 was about 10.6 minutes and the half-life of the control material (PDRN) was about 1.6 minutes, and that the half-life of the material prepared in Experimental Example 1 (Chitosan-PDRN nanoparticles) was about six times that of the control material (PDRN). That is, it was confirmed that the produced material had a longer residence time in the eyes than the control material.

Figure 11:
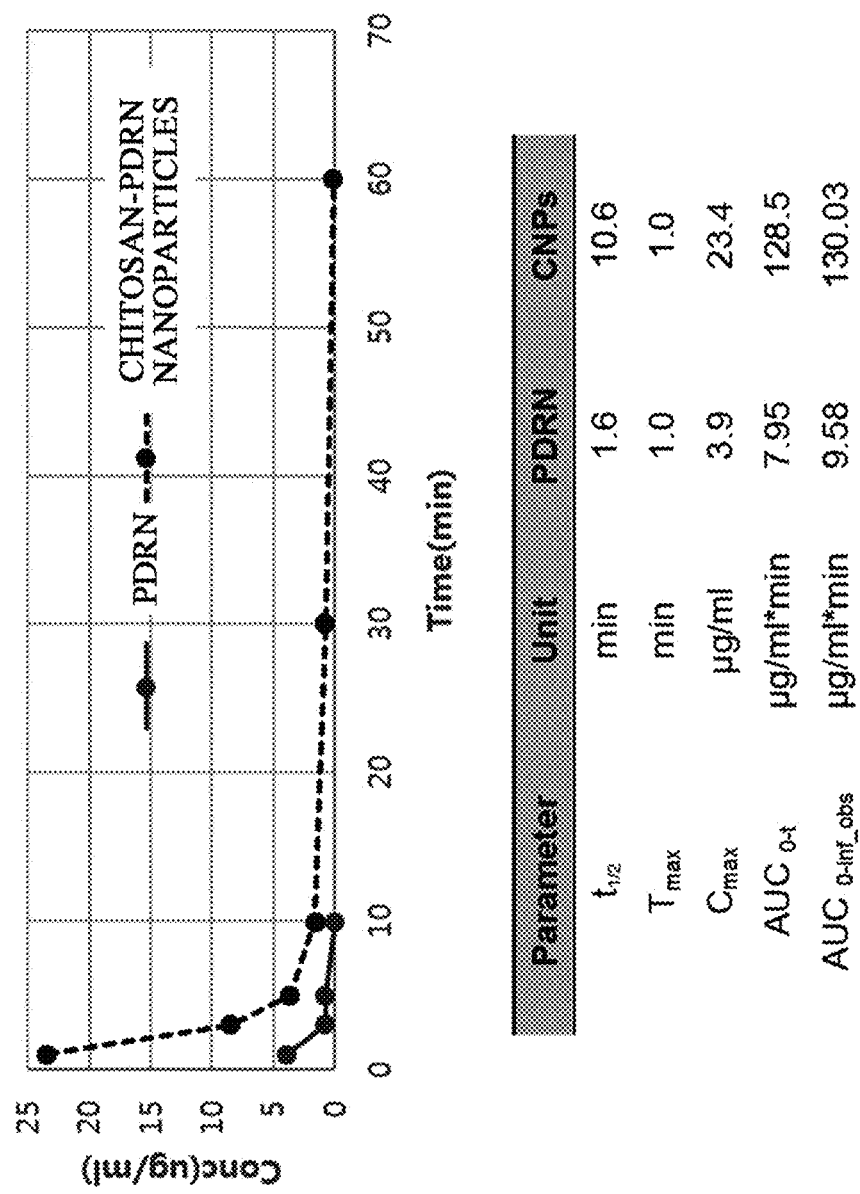
FIG. 11 shows the pharmacokinetic data of chitosan-PDRN nanoparticles.

FIG. 11 shows the pharmacokinetic data of Chitosan-PDRN nanoparticles.

From the pharmacokinetic data of FIG. 11, it can be seen that the material concentration decreased more slowly over time when the material prepared in Experimental Example 1 (Chitosan-PDRN nanoparticles) was administered than when the control material (PDRN) was administered. Furthermore, considering that the concentrations of the material prepared in Experimental Example 1 (Chitosan-PDRN nanoparticles) and the control material were 23.4 μg/mL and 3.9 μg/mL, respectively, immediately after administration, it can also be seen that the initial concentration of the material prepared in Experimental Example 1 (Chitosan-PDRN nanoparticles) was higher.

Through this, it can be seen that when PDRN-encapsulated chitosan nanoparticles are administered to the eyes, not only can a high concentration be maintained for a longer period of time than when PDRN is not encapsulated, but also the residence time of PDRN in the eyes can be increased.

That is, it can be seen that the half-life is decreased and the residence time in the eyes is increased because the material is slowly released as a result of encapsulation.

4-2. Evaluation of Cell Activity

L cell activity (ATCC® CRL-2648™) was measured using an MTT assay method that is typically known to those skilled in the art.

To measure cell viability, viability, distilled water was treated as a negative control and experimental groups were treated with chitosan-PDRN nanoparticles of various concentrations. Cell viability was measured at an absorbance of 595 nm using a microreader.

Figure 12:
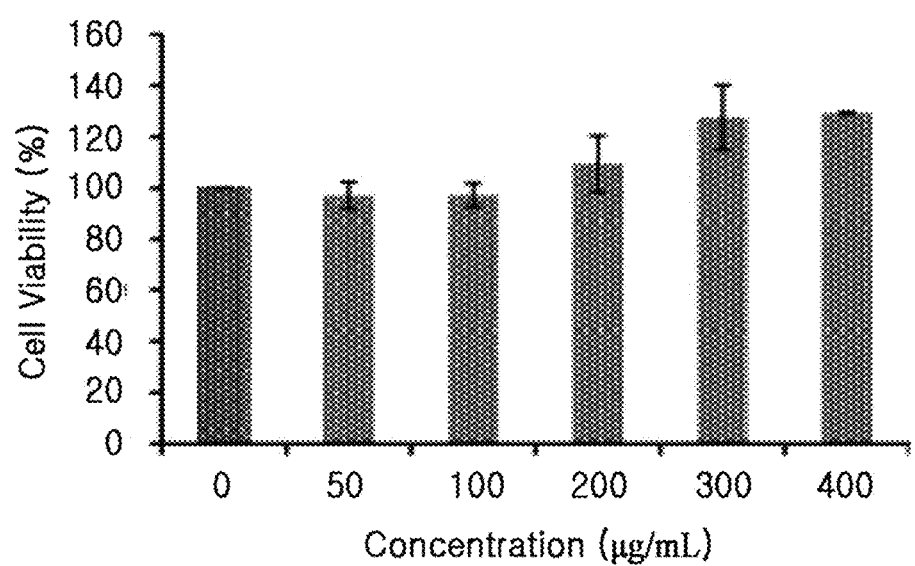
FIG. 12 shows cell viability according to chitosan-PDRN treatment.

FIG. 12 shows cell viability according to chitosan-PDRN treatment.

From the results of FIG. 12, in which cells were treated with chitosan-PDRN at a concentration of 50 μg/ml, 100 μg/ml, 200 μg/ml, 300 μg/mL, or 400 μg/mL, it can be seen that cell viability increased at concentrations of 200 m/mL or more.

4-3. Evaluation of Safety

To evaluate the occurrence of irritation of the ocular mucous membrane and the level of irritation, the present inventors pulled the rabbits' lower right eyelid away from the eyes, forming a cup-like shape, and instilled 0.1 ml of the material of Experimental Example 1 (Chitosan-PDRN nanoparticles) once into the conjunctival sac using a 1 ml syringe. Subsequently, the present inventors kept the eyes closed for about one second to prevent loss of the material of Experimental Example 1. The left eye was used as an untreated control.

FIG. 13 shows the results of evaluating the occurrence of irritation of the ocular mucous membrane due to chitosan-PDRN nanoparticles and the level of irritation.

As determined by the Kay and Calandra system, the maximum mean total score (MMTS) of the Chitosan-PDRN nanoparticles was 0 and the tested material was classified as "non-irritating" in the tentative evaluation of eye irritation. In the final evaluation, a mean total score (MTS) 24 hours after administration was "0," also indicating that the tested material was "nonirritating."

These experimental examples are only for illustrating the present invention, and it will be apparent to those of ordinary skill in the art that the scope of the present invention should not be construed as being limited by the experimental examples.

INDUSTRIAL APPLICABILITY

The present invention can provide an eye drop containing PDRN-encapsulated chitosan nanoparticles and a method for manufacturing the same.

The invention claimed is:

1. An eye drop in the form of a suspension, comprising nanoparticles, each encapsulating polydeoxyribonucleotide (PDRN),
   wherein the nanoparticles comprise chitosan and do not comprise hyaluronic acid,
   wherein the nanoparticles are mucosa-adhesive,
   wherein the nanoparticles are suspended in at least one selected from distilled water, an organic solvent, and a mixture thereof, and
   wherein the concentration of the nanoparticles in the eye drop is 200 µg/ml to 400 µg/ml.

2. The eye drop of claim 1, wherein the nanoparticles further comprise tripolyphosphate.

3. The eye drop of claim 1, wherein the PDRN is derived from a fish, animal, or plant.

4. The eye drop of claim 3, wherein the fish is salmonid.

5. The eye drop of claim 1, wherein the length of the PDRN is 50 bp to 750 bp.

6. The eye drop of claim 1, wherein the PDRN is a single-stranded nucleic acid fragment or double-stranded nucleic acid fragment.

7. The eye drop of claim 1, wherein the nanoparticles have a diameter of 100 nm to 1000 nm.

8. The eye drop of claim 1, wherein the eye drop comprises 0.6 mg/ml to 10 mg/ml of the PDRN.

9. The eye drop of claim 1, wherein the mucosa is at least one selected from intraocular mucosa, oral mucosa, nasal mucosa, anal mucosa, and vaginal mucosa.

10. A method for preparing the eye drop of claim 1, wherein the method comprises:
    preparing a chitosan solution by mixing chitosan and water;
    preparing a PDRN solution by dissolving PDRN in water;
    preparing a mixed solution by mixing the chitosan solution and the PDRN solution;
    shearing the mixed solution at high pressure to be dispersed to obtain the chitosan nanoparticles; and
    mixing the chitosan nanoparticles with at least one selected from distilled water, an organic solvent, and a mixture thereof.

11. The method of claim 10, wherein the shearing is performed by using a high-pressure disperser.

12. The method of claim 10, wherein the shearing is processed under pressure conditions of 10,000 psi to 20,000 psi.

13. The method of claim 10, wherein the preparing a PDRN solution further comprises adding 0.005 g to 0.01 g of tripolyphosphate.

* * * * *